United States Patent [19]

Miyahara et al.

[11] Patent Number: 4,733,009

[45] Date of Patent: Mar. 22, 1988

[54] METHOD FOR SEPARATING GLYCINE AND L-SERINE FROM A SOLUTION CONTAINING SAME

[75] Inventors: Shoichiro Miyahara; Toshio Matsumoto; Tooru Miyahara; Akio Sakaguchi; Kazunari Nitta, all of Omuta, Japan

[73] Assignee: Mitsui Toatsu Chemicals, Incorporated, Tokyo, Japan

[21] Appl. No.: 886,160

[22] Filed: Jul. 16, 1986

[30] Foreign Application Priority Data

Jul. 29, 1985 [JP] Japan .................................. 60-165936

[51] Int. Cl.$^4$ ............................................. C07C 99/12
[52] U.S. Cl. .................................................... 562/554
[58] Field of Search ......................... 562/554, 567, 575

[56] References Cited

U.S. PATENT DOCUMENTS 3,505,399 4/1970 Samejima ............................ 562/554

FOREIGN PATENT DOCUMENTS

| 3326633 | 1/1985 | Fed. Rep. of Germany ...... 562/554 |
| 58-172352 | 10/1983 | Japan .................................... 562/554 |
| 693522 | 7/1953 | United Kingdom ................ 562/554 |

OTHER PUBLICATIONS

Greenstein, "Chemistry of the Amino Acids", vol. 2, pp. 1452–1477 & 1500–1511 (1961).

Primary Examiner—Michael L. Shippen
Attorney, Agent, or Firm—Oblon, Fisher, Spivak, McClelland & Maier

[57] ABSTRACT

Disclosed is a method for separating lycine and L-serine from a solution containing both of them in the dissolved state and, in particular, a reaction solution obtained from a fermentation or enzymic conversion process for the preparation of L-serine by using glycine as the raw material. This method is based on a chromatographic technique utilizing the differential affinity of L-serine and glycine for a strongly acidic ion exchange resin.

9 Claims, 3 Drawing Figures

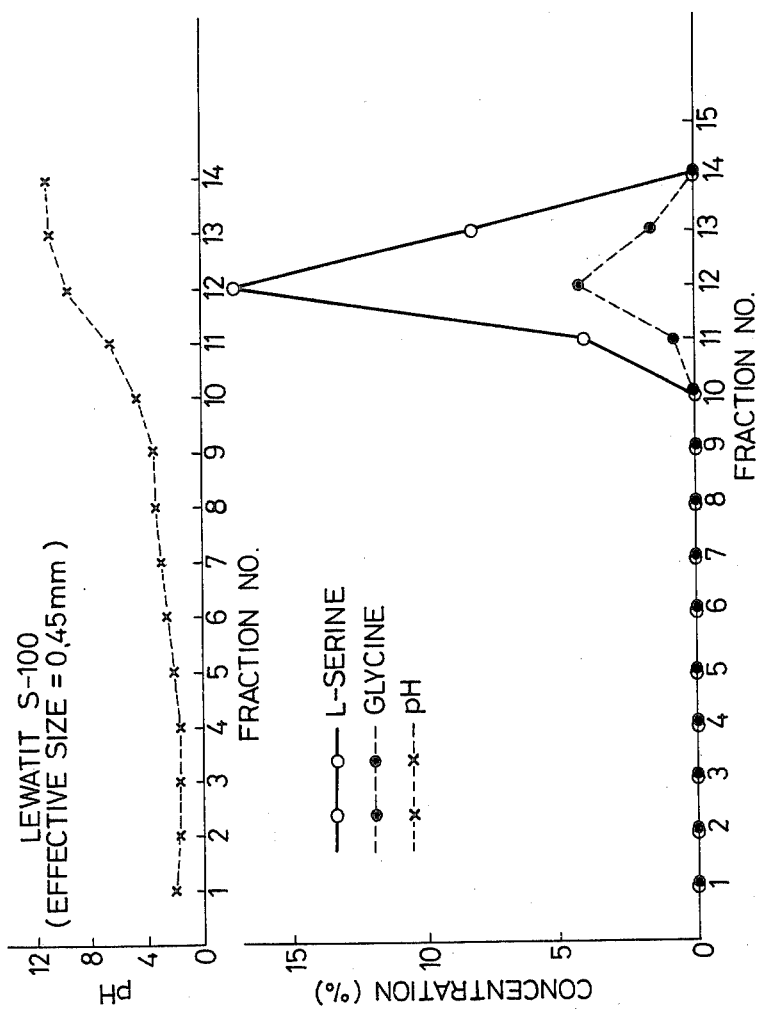

METHOD FOR SEPARATING GLYCINE AND L-SERINE FROM A SOLUTION CONTAINING SAME

BACKGROUND OF THE INVENTION (1) Field of the Invention

This invention relates to a method for separating glycine and L-serine from a solution containing both of them. More particularly, it relates to a method for isolating and recovering the L-serine formed by a fermentation or enzymic conversion process using glycine as the raw material.

L-serine is a compound useful as a constituent of solutions for use in infusion, as a raw material of the preparation of drugs, and as an intermediate for the synthesis of amino acids such as tryptophan and the like.

(2) Description of the Prior Art

A large number of processes for the preparation of L-serine by using glycine as the raw material are known. They include, for example, enzymic conversion processes such as a process for preparing L-serine from glycine and formalin in the presence of tetrahydrofolic acid as a coenzyme by using a microorganism capable of producing L-serine hydroxymethyltransferase (E.C. 2.1.2.1) (Japanese patent Laid-Open No. 81691/'78) and a process for the preparation of L-serine by bringing glycine into contact with a microorganism capable of converting glycine to L-serine and then recovering the L-serine so formed (Japanese patent Laid-Open No. 130490/'78); processes for the preparation of L-serine by growing a microorganism in a glycine-containing medium so as to accumulate L-serine in the medium (Japanese patent Laid-Open Nos. 31995/'83, 88798/'81, 37169/'80, 29906/80, 26875/'80 and 72893/'78); and the like.

However, such processes for the preparation of L-serine by using glycine as the raw material involve difficulty in separating the L-serine formed as a reaction product from the glycine remaining in the reaction solution.

For example, where glycine is converted to L-serine by means of an enzyme such as L-serine hydroxymethyltransferase or the like, this conversion is based on an equilibrium reaction in which the degree of conversion of glycine to L-serine is always not greater than 75% and usually not greater than 50%. Accordingly, the resulting reaction solution always contains both glycine and L-serine, which are very difficult to separate.

Since the solubility of glycine in water (22% at 20° C. in the neutral pH range) is very close to that of L-serine (18%), it is very difficult to separate only one of them from the reaction solution by utilizing the difference in solubility between them.

For that reason, the aforementioned Japanese patent Laid-Open No. 31995/'83 discloses a method for the isolation of L-serine by utilizing the difference in solubility in the m-xylene-4-sulfonic acid salts of glycine and L-serine. However, this method requires troublesome operations and fails to give a satisfactorily high yield, so that it cannot be regarded as practicable for industrial purposes.

On the other hand, a number of conventional methods for the separation of amino acids by using a strongly acidic ion exchange resin are known as described, for example, in Japanese patent Laid-Open No. 72893/'78. In the present case, however, the isoelectric point of glycine (5.97) is very close to that of L-serine (5.68). Thus, it is difficult to separate them and recover glycine by an ordinary adsorption and elution procedure based on the exchange of ions. According to the invention of the aforementioned Japanese patent, a method for the separation of glycine and L-serine has been proposed in which, on the basis of the fact that their isoelectric points change differently with the pH of the solution, they are separated by repeating their adsorption to and elution from a strongly acidic ion exchange resin while gradually varying the pH of the solution by means of a buffer such as citric acid or the like. However, this method fails to separate them satisfactorily and, moreover, requires troublesome operations. Accordingly, this method cannot be considered to be an industrially practicable one.

Thus, it has been impossible to separate glycine and L-serine efficiently, even when a strongly acidic ion exchange resin is used. For this reason, even if glycine used as the raw material can be converted to L-serine at a considerable degree of conversion, the L-serine cannot be isolated and recovered in a satisfactorily high yield. Moreover, it is unavoidable to waste an appreciable portion of the expensive glycine used as the raw material. These disadvantages eventually raise the overall product cost of L-serine.

SUMMARY OF THE INVENTION

It is one object of the present invention to provide a method for efficiently separating glycine and L-serine from a solution containing both of them.

It is another object of the present invention to provide a method for isolating L-serine, in high yield, from a solution obtained from a fermentation or enzymic conversion process for the preparation of L-serine from glycine.

It is still another object of the present invention to provide a method for efficiently separating glycine and L-serine from a solution obtained from a fermentation or enzymic conversion process for the preparation of L-serine from glycine wherein the glycine so separated can be reused as a raw material so as to allow a substantial reduction in the production cost of L-serine.

In order to accomplish the above-described objects, the present inventors have made an intensive investigation and have devised the method of the present invention on the basis of the following findings.

Specifically, it has been found that, although glycine and L-serine have little difference in solubility in water or isoelectric point, glycine has a greater affinity for a certain ion exchange resin than L-serine. That is, if a solution containing both glycine and L-serine is passed through a column packed with a strongly acidic ion exchange resin having a specific particle size and a specific particle size distribution, under such conditions as to induce chromatographic development, the glycine is easily retained by the resin while the L-serine is less easily retained thereby. Accordingly, glycine and L-serine can be relatively easily separated by utilizing these properties.

More specifically, if a strongly acidic ion exchange resin having an effective size of 0.15 to 0.40 mm and a uniformity coefficient of not greater than 1.7 is used in the treatment of a solution containing both glycine and L-serine, they can be easily separated by chromatographic development.

Thus, the present invention provides a method for separating glycine and L-serine from a solution thereof which comprises the steps of passing a solution containing both glycine and L-serine in the dissolved state through a column of a strongly acidic ion exchange resin having an effective size of 0.15 to 0.40 mm and a uniformity coefficient of not greater than 1.7 at a linear velocity of not greater than 2 meters per hour to obtain an effluent containing the L-serine while retaining the glycine within the column, and then bringing an alkaline solution into contact with the column to obtain an eluate containing the glycine.

BRIEF DESCRIPTION OF THE DRAWINGS

FIG. 3 is a plot of the same parameters of each of the fractions obtained in Comparative Example.

DETAILED DESCRIPTION OF THE INVENTION AND THE PREFERRED EMBODIMENTS

Figure 1:
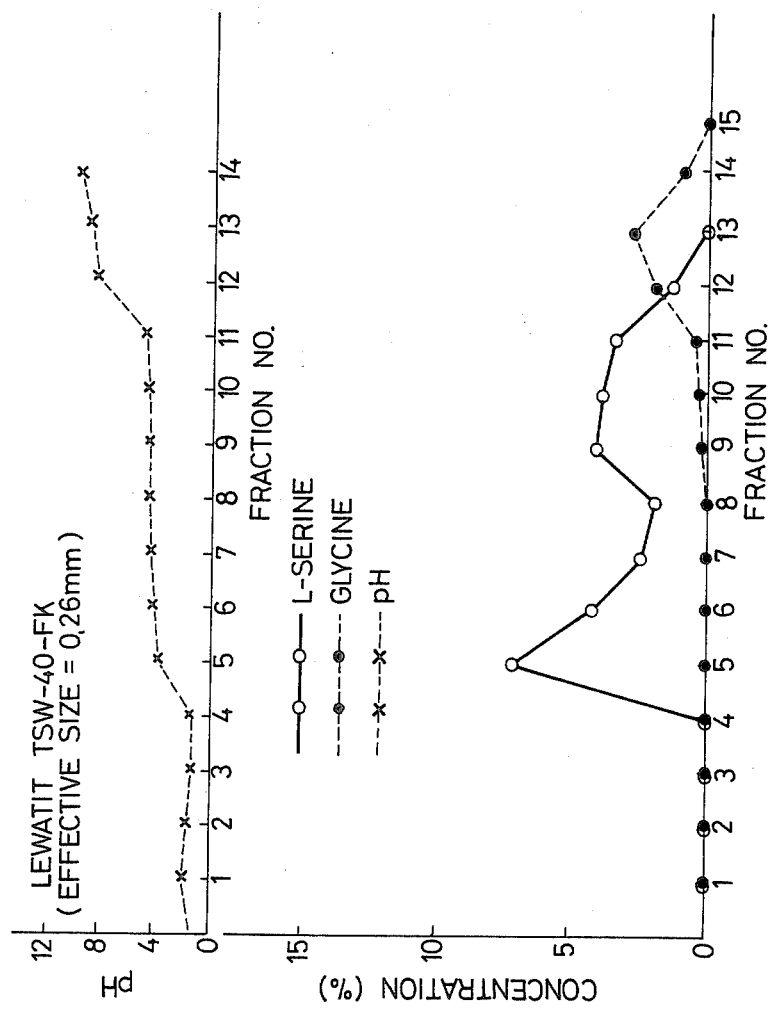
FIGS. 1 and 2 are plots of the pH, L-serine concentration and glycine concentration of each of the fractions obtained in Examples 1 and 2 in which a reaction solution and subsequently an eluent were passed through a column packed with an ion exchange resin and the resulting effluent was collected in 500 g fractions over the period extending from the start of the passage of the reaction solution to the end of the passage of the eluent.

In the practice of the present invention, a solution containing both glycine and L-serine is passed through a column packed with a strongly acidic ion exchange resin, so that an L-serine fraction is obtained as the effluent from the column. On the other hand, a glycine fraction is obtained as the eluate produced by bringing an alkaline solution into contact with the column. From the L-serine fraction thus obtained, L-serine of high quality can be isolated by conventional crystallization procedure. The glycine fraction may be used to isolate and recover the glycine by resorting to any desired means. However, where the present invention is applied to the preparation of L-serine by using glycine as the raw material, the above glycine fraction can be directly recycled to the reaction system for the conversion of glycine to L-serine, and this recycling brings about a marked improvement in the degree of conversion of glycine to L-serine.

The strongly acidic ion exchange resin used in the method of the present invention must be a cation exchange resin having an effective size of 0.15 to 0.40 mm and a uniformity coefficient of not greater than 1.7. Such strongly acidic cation exchange resins are commercially available under the trade names of Lewatit TSW-40 and TSW-40-FK (products of Bayer AG.), Diaion FRK-01 (a product of Mitsubishi Chemical Industries, Ltd.) and the like.

As is conventionally defined in the art, the term "effective size" means the mesh size of a screen which allows the passage of 10% of all resin particles while preventing that of the remainder (90%). The term "uniformity coefficient" means a parameter that indicates the degree of uniformity of the particle size distribution of a resin and is defined as a value obtained dividing the mesh size of a screen which allows the passage of 60% of all resin particles while preventing that of the remainder (40%) by the effective size [i.e., the mesh size of a screen which allows the passage of 10% of all resin particles while preventing that of the remainder (90%)].

Accordingly, the particles size distribution becomes more uniform as the uniformity coefficient approaches 1.

In the practice of the present invention, the use of a resin having an effective size smaller than 0.15 mm will enhance the separation efficiency, but may cause some difficulties from an industrial point of view. They include, for example, an increase in pressure loss of the resin bed due to its clogging with the foreign matter present in the reaction solution, and a reduction in physical durability of the resin due to the passage of an acid solution for reconverting the resin (having been in contact with the alkaline solution) to the $H^+$ form. On the other hand, if the effective size is larger than 0.40 mm, the difference in affinity for the resin between glycine and L-serine may fail to manifest itself, resulting in a decrease in chromatographic separating effect. Similarly, if the uniformity coefficient is greater than 1.7 (i.e., the resin has an undesirably wide particle size distribution), the objects of the present invention cannot be accomplished because of a descrease in chromatographic separating effect.

No limitation is placed on the concentrations and proportions of L-serine and glycine contained in the solution to be treated. Thus, the method of the present invention permits a solution containing L-serine and glycine at any desired concentrations lower than their saturation concentrations and in any desired proportions to be passed through the column as the solution to be treated.

The amount of resin used should be such that the total amount of cations present in the solution to be treated (i.e., the total capacity of L-serine, glycine and other cationic components usually present in the reaction solution, such as contaminative amino acids, potassium ions, ammonium ions, sodium ions and the like) is within the limit of the total exchange capacity of the resin.

The resin is packed into a column and then converted to the $H^+$ form by washing with dilute hydro-chloric acid. The optimum height of the resin bed depends on the linear velocity (L.V.) and glycine content of the solution to be treated. However, in order to achieve a good separation efficiency, it is usually desirable to pass the solution through the column in a volume equal to or larger than that of the resin bed. In such a case, the height of the resin bed should be 1000 mm or greater. Moreover, the solution to be treated should be passed through the column at a linear velocity of not greater than 2 meters per hour and preferably not greater than 1 meter per hour. If the linear velocity of the solution to be treated is greater than 2, it will not be suitable for purposes of chromatographic separation. Furthermore, the solution to be treated should be passed through the column at a temperature of 60° C. or below.

After the passage of the solution to be treated, the resin bed is washed by passing therethrough an equal or larger volume of water at a linear velocity of not greater than 2 meters per hour and thus displacing the solution retained within the column.

As a result of the above operation, an L-serine-rich fraction is obtained as the effluent.

Thereafter, an eluent comprising an alkaline solution is brought into contact with the resin bed to elute the glycine retained within the column, so that a glycine-rich fraction is obtained as the eluate. The alkaline solution may be selected from various types of alkaline solutions that are commonly used to convert the resin to the alkaline form. However, if it is desired to use the eluate directly as a raw material for the conversion of glycine to L-serine, it is desirable to use aqueous ammonia. The alkaline solution should preferably have a concentration of the order of 0.1 to 5%. Among others, an alkaline solution having a concentration of about 1% is especially preferred for use as the eluent.

From the L-serine-rich fraction thus obtained, L-serine crystals can be isolated according to any conventional concentration and crystallization procedure. On the other hand, the glycine-rich fraction may be directly used as a raw material for the conversion of glycine to L-serine. Of course, it is not precluded to isolate glycine from the fraction by resorting to any desired means.

EXAMPLE 1

In the presence of serine hydroxymethyltransferase produced by the culture of *Escherichia coli*, glycine and formalin (formaldehyde) were allowed to interact in an aqueous medium containing tetrahydrofolic acid and pyridoxal phosphate as coenzymes. Thus, there was obtained 571 g of a reaction solution containing 26.0% of L-serine and 6.1% of glycine. On the other hand, a column was packed with 1.9 liters of a strongly acidic cation exchange resin, or Lewatit TSW-40-FK (having an effective size of 0.26 mm and a uniformity coefficient of 1.7), so as to form a resin bed (H+ form) having a height of 1100 mm and a diameter of 48 mm. The above reaction solution was heat-treated to deactivate the enzyme, and then fed to the top of the column at such a rate as to give a space velocity of 1 (or a linear velocity of 0.8 meter per hour).

After completion of the feeding of the reaction solution, 3500 ml of deionized water was passed, from top, through the column at a space velocity of 1 (or a linear velocity of 0.8 meter per hour). Subsequently, 6000 ml of 1% aqueous ammonia was passed through the column at a space velocity of 2, and finally, 1500 ml of deionized water was passed through the column to wash the resin bed. From the start of the passage of the reaction solution, the effluent was collected in 500 g fractions throughout the passage of the reaction solution, the washing with deionized water (Fraction Nos. 5 to 11) and the elution with aqueous ammonia (Fraction No. 12 and onward). The pH, L-serine concentration (%) and content (g), and glycine concentration (%) and content (g) of each of the fractions thus obtained are shown in Table 1. Moreover, the pH, L-serine concentration (%) and glycine concentration (%) of each fraction are plotted in FIG. 1.

TABLE 1

| Fraction No. | pH | L-serine % (g) | Glycine % (g) |
|---|---|---|---|
| 1 | 2.0 | 0 | 0 |
| 2 | 1.9 | 0 | 0 |
| 3 | 1.6 | 0 | 0 |
| 4 | 1.6 | 0 | 0 |
| 5 | 4.2 | 7.2 (36.0) | 0 |
| 6 | 4.6 | 4.2 (21.0) | 0 |
| 7 | 4.8 | 2.4 (12.0) | 0 |
| 8 | 5.0 | 2.0 (10.0) | 0 |
| 9 | 5.2 | 4.2 (21.0) | 0.2 (1) |
| 10 | 5.4 | 4.0 (20.0) | 0.3 (1.5) |
| 11 | 5.4 | 3.5 (17.5) | 0.4 (2.0) |
| 12 | 8.4 | 1.5 (7.5) | 2.0 (10.0) |
| 13 | 9.4 | 0.2 (1.0) | 3.0 (15.0) |
| 14 | 10.0 | 0 | 1.0 (5.0) |
| 15 | 11.0 | 0 | 0 |

The L-serine and glycine concentrations of each fraction were determined by high-speed liquid chromatography using the following analytical conditions.

Column: SHODEX OH Pack B-804 (a product of Showa Denko Co., Ltd.).
Mobile phase: 5 mM aqueous solution of phosphoric acid.
Column temperature: Room temperature.
Flow rate: 1.0 ml/min.
Detector: Infrared detector.
Retention time (R.T.) under the aforesaid measuring conditions:
L-serine: 27.9 minutes.
Glycine: 31.7 minutes.
L-serine fraction: Fraction Nos. 5-11 (3500 g in total).
L-serine: 137.5 g (92.6% of the fed L-serine).
Glycine: 4.5 g (12.9% of the fed glycine).
Glycine fraction: Fraction Nos. 12-14 (1500 g in total).
L-serine: 8.5 g (5.7% of the fed L-serine).
Glycine: 30.0 g (86.1% of the fed glycine).

The above 3500 g L-serine fraction (containing 3.9% of L-serine) was concentrated to 275 g so as to give an L-serine concentration of about 20%. After the addition of 275 g of isopropyl alcohol, the resulting mixture was cooled and the precipitate so formed was filtered off and dried to obtain 118 g of L-serine crystals (in a separation yield of 85.8%). This product had a purity of 99.8% and a specific optical rotation, $[\alpha]_{20}^D$, of +14.6, indicating satisfactory results.

EXAMPLE 2

In the presence of serine hydroxymethyltransferase produced by the culture of *Escherichia coli*, glycine and formalin (formaldehyde) were allowed to interact in an aqueous medium containing tetrahydrofolic acid and pyridoxal phosphate as coenzymes. Thus, there was obtained 571 g of a reaction solution containing 26.0% of L-serine and 6.1% of glycine. On the other hand, a column was packed with 1.9 liters of a strongly acidic cation exchange resin (having an effective size of 0.38 mm and a uniformity coefficient of 1.7) so as to form a resin bed (H+ form) having a height of 1100 mm and a diameter of 48 mm. The above reaction solution was heat-treated to deactivate the enzyme, and then fed to the top of the column at such a rate as to give a space velocity of 1 (or a linear velocity of 0.8 meter per hour).

Figure 2:
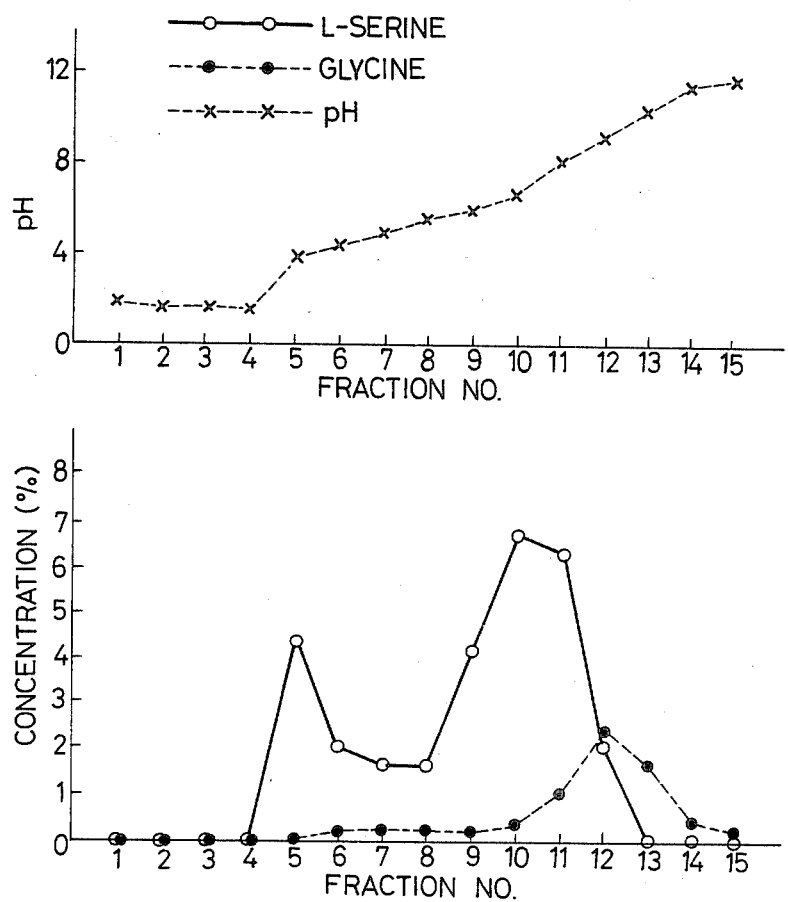

After completion of the feeding of the reaction solution, 3500 ml of deionized water was passed, from top, through the column at a space velocity of 1 (or a linear velocity of 0.8 meter per hour). Subsequently, 6000 ml of 1% aqueous ammonia was passed through the column at a space velocity of 2, and finally, 1500 ml of deionized water was passed through the column to wash the resin bed. From the start of the passage of the reaction solution, the effluent was collected in 500 g fractions throughout the passage of the reaction solution, the washing with deionized water (Fraction Nos. 5 to 11) and the elution with aqueous ammonia (Fraction No. 12 and onward). The pH, L-serine concentration (%) and content (g), and glycine concentration (%) and content (g) of each of the fractions thus obtained are shown in Table 2. Moreover, the pH, L-serine concentration (%) and glycine concentration (%) of each fraction are plotted in FIG. 2.

TABLE 2

| Fraction No. | pH | L-serine % (g) | Glycine % (g) |
| --- | --- | --- | --- |
| 1 | 1.9 | 0 | 0 |
| 2 | 1.8 | 0 | 0 |
| 3 | 1.8 | 0 | 0 |
| 4 | 1.6 | 0 | 0 |
| 5 | 3.8 | 4.4 (22.0) | 0 |
| 6 | 4.4 | 2.0 (10.0) | 0.2 (1.0) |
| 7 | 5.0 | 1.6 (8.0) | 0.2 (1.0) |
| 8 | 5.6 | 1.6 (8.0) | 0.2 (1.0) |
| 9 | 6.0 | 4.2 (21.0) | 0.2 (1.0) |
| 10 | 6.8 | 6.8 (34.0) | 0.3 (1.5) |
| 11 | 8.2 | 6.4 (32.0) | 1.0 (5.0) |
| 12 | 9.2 | 2.0 (10.0) | 2.4 (12.0) |
| 13 | 10.4 | 0 | 1.6 (8.0) |
| 14 | 11.6 | 0 | 0.4 (2.0) |
| 15 | 11.8 | 0 | 0.2 (1.0) |

L-serine fraction: Fraction Nos. 5-11 (3500 g in total).
L-serine: 135.0 g (90.9% of the fed L-serine).
Glycine: 10.5 g (30.2% of the fed glycine).
Glycine fraction: Fraction Nos. 12-15 (2000 g in total).
L-serine: 10.0 g (6.7% of the fed L-serine).
Glycine: 23.0 g (66.1% of the fed glycine).

The above 3500 g L-serine fraction (containing 3.9% of L-serine) was concentrated to 275 g so as to give an L-serine concentration of about 20%. After the addition of 275 g of isopropyl alcohol, the resulting mixture was cooled and the precipitate so formed was filtered off and dried to obtain 114 g of L-serine crystals (in a separation yield of 84.4%). This product had a purity of 99.9% and a specific optical rotation, $[\alpha]_{20}^D$, of +15.0, indicating satisfactory results.

COMPARATIVE EXAMPLE 571 g of a reaction solution was obtained in the same manner as described in Example 1. On the other hand, a column was packed with 1.9 liters of a strongly acidic cation exchange resin, or Lewatit S-100 (a product of Bayer AG., having an effective size of 0.45 mm and a uniformity coefficient of 1.8 or less), so as to form a resin bed (H+ form) having a height of 1100 mm and a diameter of 48 mm. The above reaction solution was heat-treated to deactivate the enzyme, and then fed to the top of the column under the same conditions as used in Example 1, i.e., at such a rate as to give a space velocity of 1 (or a linear velocity of 0.8 meter per hour). After completion of the feeding of the reaction solution, 3500 ml of deionized water was passed, from top, through the column at a space velocity of 1 (or a linear velocity of 0.8 meter per hour). Subsequently, 6000 ml of 1% aqueous ammonia was passed through the column at a space velocity of 2, and finally, 1500 ml of deionized water was passed through the column to wash the resin bed. The analytical values of each of the fractions collected in the same manner as described in Example 1 are shown in Table 3 and FIG. 3. It may be seen from these data that glycine and L-serine were not separated in this case.

TABLE 3

| Fraction No. | pH | L-serine % (g) | Glycine % (g) |
| --- | --- | --- | --- |
| 1 | 1.8 | 0 | 0 |
| 2 | 1.7 | 0 | 0 |
| 3 | 1.6 | 0 | 0 |
| 4 | 1.6 | 0 | 0 |
| 5 | 2.0 | 0 | 0 |
| 6 | 2.4 | 0 | 0 |
| 7 | 3.0 | 0 | 0 |
| 8 | 3.5 | 0 | 0 |
| 9 | 3.8 | 0 | 0 |
| 10 | 4.6 | 0 | 0 |
| 11 | 6.4 | 4.0 (20) | 0.8 (4) |
| 12 | 9.8 | 16.8 (84) | 4.2 (21) |
| 13 | 11.6 | 8.2 (41) | 1.6 (8) |
| 14 | 11.6 | 0 | 0 |
| 15 | | 0 | 0 |

Fractions Nos. 11-13 (1500 g in total)
L-serine: 145.0 g (97.6% of the fed L-serine).
Glycine: 33.0 g (94.8% of the fed glycine).

The above 1500 g fraction (containing 9.7% of L-serine and 2.2% of glycine) was concentrated to 290 g so as to give an L-serine concentration of about 20%. After the addition of 290 g of isopropyl alcohol, the resulting mixture was cooled and the precipitate so formed was filtered off and dried to obtain 132 g of crystals. This product had an L-serine concentration of 87.8% and was contaminated with 10.2% of glycine.

We claim:
1. A method for separating glycine and L-serine from a solution thereof which comprises:
   (a) passing a solution containing both glycine and L-serine in the dissolved state through a column of a strongly acidic ion exchange resin having an effective size of 0.15 to 0.40 mm and a uniformity coefficient of not greater than 1.7 at a linear velocity of not greater than 2 meters per hour, followed by passing water through the column at a linear velocity of not greater than 2 meters per hour to obtain an effluent fraction containing a substantial portion of said L-serine charged as an effluent, while retaining the glycine within the column, and then
   (b) bringing an alkaline solution into contact with the column to obtain an eluate containing substantially all of said glycine.
2. The method as claimed in claim 1 wherein the solution containing both glycine and L-serine is a solution obtained from a fermentation or enzymatic conversion process using glycine as the raw material and containing a mixture of unreacted glycine and formed L-serine.
3. The method as claimed in claim 1 wherein the solution is passed through the column at a linear velocity of not greater than 1 meter per hour.
4. The method as claimed in claim 1, wherein the amount of resin used is such that the total amount of cations present in the solution to be treated is within the limit of the total exchange capacity of the resin.
5. The method as claimed in claim 1, which further comprises, prior to passing the solution containing glycine and L-serine through the column, washing the column with dilute hydrocloric acid.
6. The method as claimed in claim 1, wherein said column of strongly acidic ion exchange resin has a resin bed of at least 1000 mm in height.
7. The method as claimed in claim 1, wherein said solution containing glycine and L-serine is passed through the column at a temperature of 60° C. or below.
8. The method as claimed in claim 1, wherein said alkaline solution is aqueous ammonia having a concentration of about 0.1 to 5%.
9. The method as claimed in claim 8, wherein said aqueous ammonia has a concentration of about 1%.

* * * * *